United States Patent
Boudaden et al.

(10) Patent No.: US 11,435,308 B2
(45) Date of Patent: Sep. 6, 2022

(54) CO2 SENSOR AND METHOD FOR MANUFACTURING SAME

(71) Applicant: Fraunhofer-Gesellschaft zur Foerderung der angewandten Forschung e.V., Munich (DE)

(72) Inventors: Jamila Boudaden, Munich (DE); Benjamin Gruber, Regensburg (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 321 days.

(21) Appl. No.: 16/053,506

(22) Filed: Aug. 2, 2018

(65) Prior Publication Data

US 2018/0372662 A1 Dec. 27, 2018

Related U.S. Application Data (63) Continuation of application No. PCT/EP2017/052430, filed on Feb. 3, 2017.

(30) Foreign Application Priority Data

Feb. 4, 2016 (EP) .................... 16154283

(51) Int. Cl.
*G01N 27/12* (2006.01)
*G01N 33/00* (2006.01)
(Continued)

(52) U.S. Cl.
CPC ......... *G01N 27/126* (2013.01); *G01N 21/359* (2013.01); *G01N 27/127* (2013.01); *G01N 27/227* (2013.01); *G01N 29/022* (2013.01); *G01N 33/004* (2013.01); *B82Y 15/00* (2013.01); *B82Y 20/00* (2013.01); *G01N 2291/0215* (2013.01); *G01N 2291/02809* (2013.01)

(58) Field of Classification Search
None
See application file for complete search history.

(56) References Cited

U.S. PATENT DOCUMENTS

2006/0293169 A1 12/2006 Srinivasan et al.
2013/0294991 A1 11/2013 Jones et al.

FOREIGN PATENT DOCUMENTS

WO   2005026694 A2   3/2005
WO   2008021700 A1   2/2008

OTHER PUBLICATIONS

C.Willa, et al., "When Nanoparticles meet Poly(Ionic Liquid)s: Chemoresistive CO2 Sensing at Room Temperature", Advanced Functional Materials, 25(17): p. 2537-2542, May (Year: 2015).*
(Continued)

*Primary Examiner* — J. Christopher Ball
(74) *Attorney, Agent, or Firm* — Perkins Coie LLP; Michael A. Glenn (57) ABSTRACT

A sensor device for sensing $CO_2$ comprises a hybrid sensing material and a transducer. The hybrid sensing material comprises at least amines and nanoparticles, wherein the hybrid sensing material has a property and is configured to change the property dependent on a current $CO_2$ concentration in the surrounding. The transducer is configured to output an electrical sensor signal dependent on the property of the hybrid sensing material.

26 Claims, 6 Drawing Sheets

(51) Int. Cl.
    *G01N 21/359*     (2014.01)
    *G01N 29/02*     (2006.01)
    *G01N 27/22*     (2006.01)
    *B82Y 15/00*     (2011.01)
    *B82Y 20/00*     (2011.01)

(56) References Cited

OTHER PUBLICATIONS

R. P. Tandon, et al. "Gas and humidity response of iron oxide—polypyrrole nanocomposites", Sensors and Actuators B: Chemical, 114(2): p. 768-773, Apr. 2006.*

"European F-Gas Regulation", (2014), URL: http://ec.europa.eu/clima/policies/fgas/index_en.htm, 2014.

"Europes Energy Union Needs Carbon Capture and Storage", http://www.euractiv.com/sections/energy/europes-energy-union-needs-carbon-capture-and-storage-312387.

Fine, George F. et al., "Metal Oxide Semi-Conductor Gas Sensors in Environmental Monitoring", Sensors 2010, 10, 5469-5502, Jun. 1, 2010, pp. 5469-5502.

Gravenstein, Nikolaus et al., "Factors Influencing Capnography and the Bain Circuit", Sep. 27, 1984.

Hodgkinson, Jane et al., "Non-dispersive infra-red (NDIR) measurement of carbon dioxide at 4.2um in a compact and optically efficient sensor.", V. 186 (2013) p. 580-588, 2013, pp. 580-588.

Labeodan, Timilehin et al., "Occupancy measurement in commercial office buildings for demand-driven control applications—A survey and detection system evaluation", Energy and Buildings 93 (2015) 303-314, Feb. 17, 2015, pp. 303.314.

Moos, Ralf et al., "Solid State Gas Sensor Research in Germany—a Status Report", Sensors 2009, 9, 4323-4365, Jun. 3, 2009, pp. 4323-4365.

Srinives, Sira et al., "A miniature chemiresistor sensor for carbon dioxide", Analytica Chimica Acta; vol. 874; May 2015; pp. 54-58; XP055289721, May 2015, pp. 54-58.

Washington State University, Energy Program, "Measuring Carbon Dioxide Inside Buildings—Why is it Important?", http://www.theboc.info/pdf I Article-Measuring_C02_Inside_Buildings-Jan2013. pdf, Jan. 2013.

World Business Council for Sustainable Development, "Guidelines for Emissions Monitoring and Reporting in the Cement Industry", Mar. 2012.

Xie, Guang-Zhong et al., "QCM Sensors Based on PEI Films for CO2 Detection", Journal of Electronic Science and Technology; vol. 13; No. 2; Jun. 2015; pp. 181-187; XP055289342, Jun. 2015, pp. 181-187.

* cited by examiner

CO2 SENSOR AND METHOD FOR MANUFACTURING SAME

CROSS-REFERENCES TO RELATED APPLICATIONS

This application is a continuation of copending International Application No. PCT/EP2017/052430, filed Feb. 3, 2017, which is incorporated herein by reference in its entirety, and additionally claims priority from European Application No. EP 16154283.2, filed Feb. 4, 2016, which is incorporated herein by reference in its entirety.

BACKGROUND OF THE INVENTION

Embodiments of the present invention refer to a $CO_2$ sensor for sensing a $CO_2$ concentration and a method for manufacturing the sensor. Embodiments refer to a sensor comprising a hybrid organic-inorganic nanomaterial for carbon dioxide sensor.

Detecting and controlling carbon dioxide ($CO_2$) concentrations attract a lot of attention, because a high performance chemical sensor may be applied to various industrial and biological applications like monitoring Heating, Ventilation and Air Conditioning (HVAC) to reduce energy consumption [1], monitoring patients for disease detection at early stages, capnography [2] and continuous monitoring of emissions in industrial combustion processes [3].

For example, $CO_2$ is nowadays used in refrigerant industry for cooling computer cores and rooms. It is considered as a replacement gas for Freons (CFCs, HCFCs: hydrochlorofluorocarbons), which were considered as clean, non-toxic, odorless gases for many years. Today, however, it is known that these gases cause depletion of the atmospheric ozone layer [4]. Using compressed $CO_2$ under high pressure provides an alternative here, as the global warming potential (GWP) of $CO_2$ is negligible compared to Freon gases. Therefore, a rapid detection of $CO_2$ is indispensable to permit a leak detection in cooling systems by closing the valves in real time and prevent accidents. For these type of industrial applications, the $CO_2$ chemical sensors work as safety switches.

In our daily life, the amount of exhaled $CO_2$ could be an indicator of occupancy in rooms kept under surveillance [5]. The $CO_2$ detector is used in security field and military situations to localize the presence of human activity, like to stop human rights violations due to human trafficking and to deliver emergency aid to the localized earthquake victims.

In the last 5 years, a lot of research activities were dedicated to find an efficient way to capture and store $CO_2$. $CO_2$ capture and storage (CCS) methods are an adequate solution to retard the global warming induced by greenhouse emissions. The European nations adopted CCS as an efficient strategy to tackle climate change [6]. For this application, $CO_2$ sensors are also needed to monitor the $CO_2$ geologic reservoirs in order to detect real time leaks occurring during the $CO_2$ injection or storage.

There are only few existing devices to detect $CO_2$ in the desired environments, based on optical or resistive methods.

Optical detection based on non-dispersive infrared (NDIR) method is one well-known way to detect gases [7]. As the $CO_2$ molecule vibrates and rotates at a well-defined frequency, at which the molecule loses its symmetry and absorbs light in the wavelength range between 4.1 and 4.4 μm, the NDIR method measures the optical signal in the infrared range and permits to identify the amount of detected $CO_2$. Although the NDIR method is accurate, makes fast measurements and has a good long-term stability, its high price, large device size and high power consumption are clear disadvantages. Moreover, its software and hardware necessitate a regular calibration and cleaning to maintain the full device performance.

Another conventional method is detection by sensitive metal oxide layers [8]. These materials however inevitably show a cross sensitivity to other gases. According to literature, the development of a metal oxide sensor capable of detecting $CO_2$ below 2000 ppm also remains challenging [9]. The working principle of resistive metal oxide sensors is based on adsorbing oxygen on the metal oxide surface, which traps free electrons extracted from the conduction band of the used metal oxide sensing layer. An electron-depleted region is formed at the grain boundaries, which prevents the electron flow between the electrodes, and consequently increases the oxide layer resistance. In the case of $CO_2$ sensor, the amount of adsorbed oxygen on the layer surface is reduced due to its reaction with $CO_2$. As a result the metal oxide resistance decreases and its value can be correlated to the amount of $CO_2$. Most of the existing metal oxide based sensors involve an operating temperature higher than 100° C. in order to reach an acceptable sensitivity. Other researchers are still looking for efficient metal oxide materials, which are able to detect $CO_2$ at temperature less than 200° C., advantageously less than 100° C.

Until today, there is a lack of sensitive, reversible and stable chemical $CO_2$ gas sensor. Currently, the best long-term stability is provided by metal oxides and optical sensors. The main disadvantage of resistive and infrared methods is their high energy consumption. Therefore, there is a need for an improved approach.

SUMMARY

According to an embodiment, a sensor device for sensing $CO_2$ may have: a hybrid sensing material having a mixture of at least amines and nanoparticles, wherein the hybrid sensing material has an electrical or optical property and is configured to change the electrical or optical property dependent on a $CO_2$ concentration in the surrounding; and a transducer configured to output an electrical sensor signal dependent on the electrical or optical property of the hybrid sensing material.

According to another embodiment, a method for manufacturing a sensor device for sensing $CO_2$ may have the following steps: providing a transducer configured to output an electrical sensor signal dependent on an electrical or optical property of a hybrid sensing material; and providing the hybrid sensing material having at least amines and nanoparticles, wherein the hybrid sensing material has an electrical or optical property and is configured to change the electrical or optical property dependent on a $CO_2$ concentration in the surrounding.

Another embodiment may have a coating having a hybrid sensing material for sensing $CO_2$ having a mixture of at least amines and nanoparticles, wherein the hybrid sensing material has a electrical or optical property and is configured to change the electrical or optical property dependent on a $CO_2$ concentration in the surrounding.

Embodiments of the present invention provide a sensor device for sensing $CO_2$ comprising a hybrid sensing material and a transducer. The hybrid sensing material comprises at least amines (or polymer-amines) and nanoparticles, wherein the hybrid sensing material has a property (e.g. a dielectric constant of the material, the imaginary and/or the real part of the dielectric constant, a capacitance, a resistance, an impedance, an optical transmission, advantageously from IR to UV, a mass) and is configured to change the property dependent on a $CO_2$ concentration in the surrounding. The transducer is configured to output an electrical sensor signal dependent on the property of the hybrid sensing material.

Teachings disclosed herein are based on the finding that a material comprising amines, like primary or secondary amines, shows a reaction dependent on the current carbon dioxide concentration in the surrounding. Due to the presence of nanoparticles within the material comprising the amines, the reaction to the carbon dioxide concentration or to the carbon dioxide concentration change is improved with regard to the evaluability. As a consequence of this, the hybrid sensing material, also referred to as sensitive layer, can be evaluated using a transducer, like a capacitance sensor or an impedance sensor, which is configured to output an electrical signal dependent on the property of the hybrid sensing material resulting from the current carbon dioxide concentration. The main advantages of such sensitive layer are the following: The response and recovery times within only some seconds depending on the chosen working temperature, layer stability of at least several months without any hysteresis of the dielectric properties, high selectivity toward $CO_2$ without showing interference to $N_2$, low manufacturing and operation costs as well as miniaturized size to be widely commercialized and integrated in mobile devices.

According to further embodiments, the sensor device may comprise two electrodes, wherein at least one electrode is coupled to the hybrid sensing material, in order to detect its property indicative for the current $CO_2$ concentration. For example, the hybrid sensing material, which may have a dielectric constant as a property, may be arranged between the two electrodes, such that a capacitance (or impedance or resistance) of the two electrodes is influenced by the $CO_2$ concentration. Background thereof is that the impedance (or the conductance and/or the capacitance) is dependent on the dielectric constant of the dielectric (here the sensing layer). For example, the electrical sensor signal indicates a changed capacitance, wherein the $CO_2$ concentration is increased. The electrodes may be made of any conducting materials (for example an inorganic conductor, an organic conductor or a mixed organic/inorganic conductor), advantageously a metal or a conducting polymeric material, more advantageously a metal selected from the group of Ni, Au, Ag, Pt, or combinations thereof According to another embodiment, the sensor device may comprise a field effect transistor with a pair of source/drain regions, a channel and a gate electrode, wherein the hybrid sensing material is positioned between the channel and the gate electrode.

According to another embodiment, the sensor device may comprise a quartz crystal microbalance (QCM) comprising an upper electrode, a lower electrode and a quartz plate positioned between the upper and lower electrodes. The hybrid sensing material is positioned on the upper electrode

According to another embodiment, the sensor device may comprise surface acoustic wave (SAW) sensor that comprises a piezoelectric substrate, a first pair of interdigitated electrodes, a second pair of interdigitated electrodes. The first pair is connected to a voltage source. The hybrid sensing material is positioned on the piezoelectric substrate between the first and second pairs.

According to a further embodiment, the sensor device may comprise a light emitting device (e.g. a light emitting diode or a laser), a light receiving device (e.g. a photodiode). The hybrid sensing material is positioned between the light receiving device and the light emitting device so that the light beam emitted by the light emitting device propagates through the hybrid sensing material and is received by the light receiving device.

According to embodiments, the hybrid sensing material may comprise organic and inorganic components. In detail, the hybrid sensing material may comprise a polymer or polymer-based amines or other amines (organic compounds) in combination with (inorganic) nanoparticles. Nanoparticles (e.g. with a diameter range from 10 to 500 nm) can be functionalized with a polymer containing amine groups. The nanoparticles bring several advantages over amine-nanogroups containing polymer without nanoparticles. The loading of the matrix raises due to the increase in the surface to the volume ratio. Advantageously, in the hybrid sensing material, the ratio between the total weight of nanoparticles and the total weight of polymer-based amines is in the range from 1:5 to 5:1.

Advantageously, the amines are primary amino groups or secondary amino groups, like 3-aminopropyltrimethosysilane (APTMS), 3-Aminopro(pyl)triethoxysilane (APTES), N-[3-(trimethoxysilyl) propyl]-ethylenediamine (AEAPTS), Polypropyleneimine (PPI), mono (di)ethanolamine (MEA (DEA)), Polyethyleneimine (PEI), 2-diethylamino-ethanol (DEEA), 1,4 diaminobutane (DAB), 1,3-propanediamine (DIAP), 2,2-dimethyl-1,3-propanediamine (DMPDA), 1-piperazineethanol (HEP), 2-diisopropylamino-ethanol (DIPAE), N,N,N',N'-tetrabutyl-3-oxapentanediamide (N-TBDA), N1-methyl-1,3-Propanediamine (MAPA), Polyallylamine (PAA) and Tetraethylenepentamine (TEPA).

According to further embodiments, the hybrid sensing materials will react with $CO_2$ in accordance with the formulas:

and/or

Advantageously, the nanoparticles may be selected from $SiO_2$, $Al_2O_3$, $TiO_2$, $ZrO_2$, and the like, and combinations thereof. The nanoparticles diameter may be in the range from 10 to 500 nm, advantageously in the range from 150 nm to 400 nm.

Advantageously, the amines are selected from PEI or APTMS or APTES or TEPA and combinations thereof, and the nanoparticles are $SiO_2$.

According to further embodiments, the sensor device may comprise means for heating the hybrid sensing material. This heater enables to reach the desired working temperature of the sensor layer. The sensor device may also comprise means (e.g. a temperature sensor) for measuring the temperature of the sensor layer.

Advantageously, the sensor device may be electrically connected to a printed circuit board (PCB) as substrate and/or may be integrated with additional microdevices (e.g. a micropump).

In an alternative embodiment, the sensor device may be located on a low temperature co-fired ceramic (LTCC) board with via contacts. The sensor device may also be on a suspended membrane (made of a conducting material e.g silicon) for heating.

A further embodiment provides a method for manufacturing a sensor device for sensing $CO_2$. The method comprises the steps of providing a transducer configured to output an electrical sensor signal dependent on a property of the hybrid sensing material and providing the hybrid sensing material, e. g. on the transducer. The hybrid sensing material comprises, as discussed above, amines and nanoparticles. The nanoparticles, existing in different sizes and shapes, can be functionalized with the amino groups or with the polymer having amino groups. The obtained hybrid material demonstrates a significant $CO_2$ loading within some seconds and ensures a thermal stability between −40° C. to 250° C.

According to a further embodiment, a hybrid sensing material comprising nanoparticles and amines is provided.

According to another embodiment the hybrid sensing material and/or the device using this hybrid sensing material can distinguish between $CO_2$ $H_2O$ since same is configured to change the electrical or optical property dependent on a $H_2O$ concentration in the surrounding.

BRIEF DESCRIPTION OF THE DRAWINGS

Embodiments of the present invention will be detailed subsequently referring to the appended drawings, in which.

DETAILED DESCRIPTION OF THE INVENTION

Figure 1A:
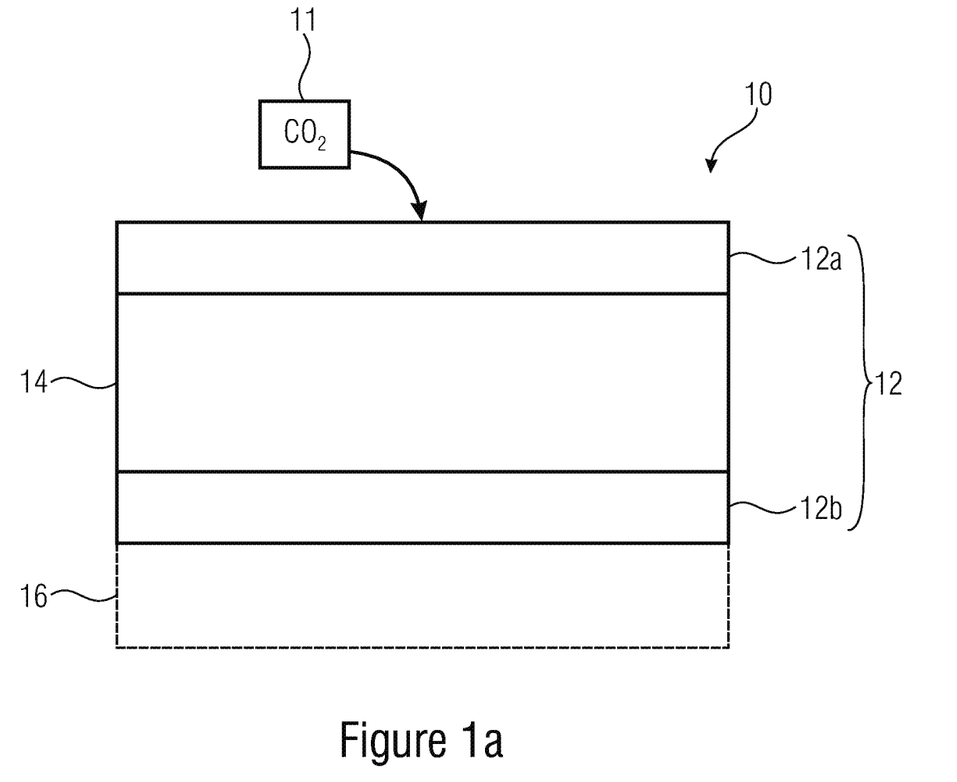
FIGS. 1a-1f show schematically sensor devices for sensing $CO_2$ according to basic embodiments.

FIG. 1a shows a sensor device 10 comprising a transducer 12 and a hybrid sensing material 14. The transducer 12 may, for example, be formed by two electrodes 12a and 12b facing each other, wherein the hybrid sensing material 14 is arranged in between. In other words this means that the hybrid sensing material 14 forms a dielectric layer having a dielectric constant. In addition, the sensitive layer 14 may be arranged on top of the electrode 12a.

The electrodes 12a and 12b may be made of any conducting materials (for example an inorganic conductor, an organic conductor or a mixed organic/inorganic conductor), advantageously a metal or a conducting polymeric material, more advantageously a metal selected from the group of Ni, Au, Ag, Pt, or combinations thereof The sensitive layer 14 changes its property, e.g., its dielectric behaviour by modifying the $CO_2$ concentration 11 present in the surrounding environment. The transducer 12 transforms the received chemical information, here the changed dielectric constant, from the sensitive layer 14 into a measurable electrical signal. This may be based, for example, on the principle that the two electrodes 12a and 12b may form a capacitive sensor having the sensitive layer 14 in between which form the dielectric layer. Due to the change of the dielectric behaviour of the sensitive layer 14, the capacitance or impedance of the sensor device is changed so an electrical signal indicative for the capacitance or the impedance may be output by the transducer.

In this context it should be noted that the sensitive layer 14 is in contact to the $CO_2$ 11 included by the surrounding. For example, the electrode 12a in FIG. 1a may be perforated or may have an opening to the surrounding for the $CO_2$ 11. Electrodes 12a and 12b in FIG. 1a may have a comb-like shape and may be interdigitated.

Figure 1B:
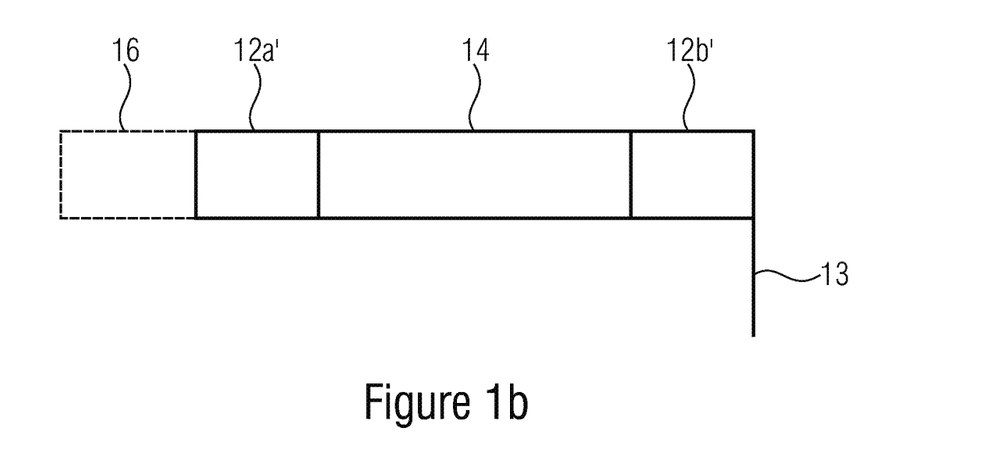

FIG. 1b shows an alternative sensor device comprising a transducer 12' and a hybrid sensing material 14 laterally arranged within a common layer. Again, the transducer 12' may, for example, be formed by two electrodes 12a' and 12b' positioned on a substrate 13, wherein the hybrid sensing material 14 is arranged in between. Electrodes 12a' and 12b' in FIG. 1b may have a comb-like shape and may be interdigitated. Additionally, the hybrid sensing material may at least partially cover electrodes 12a' and 12b'.

Figure 1C:
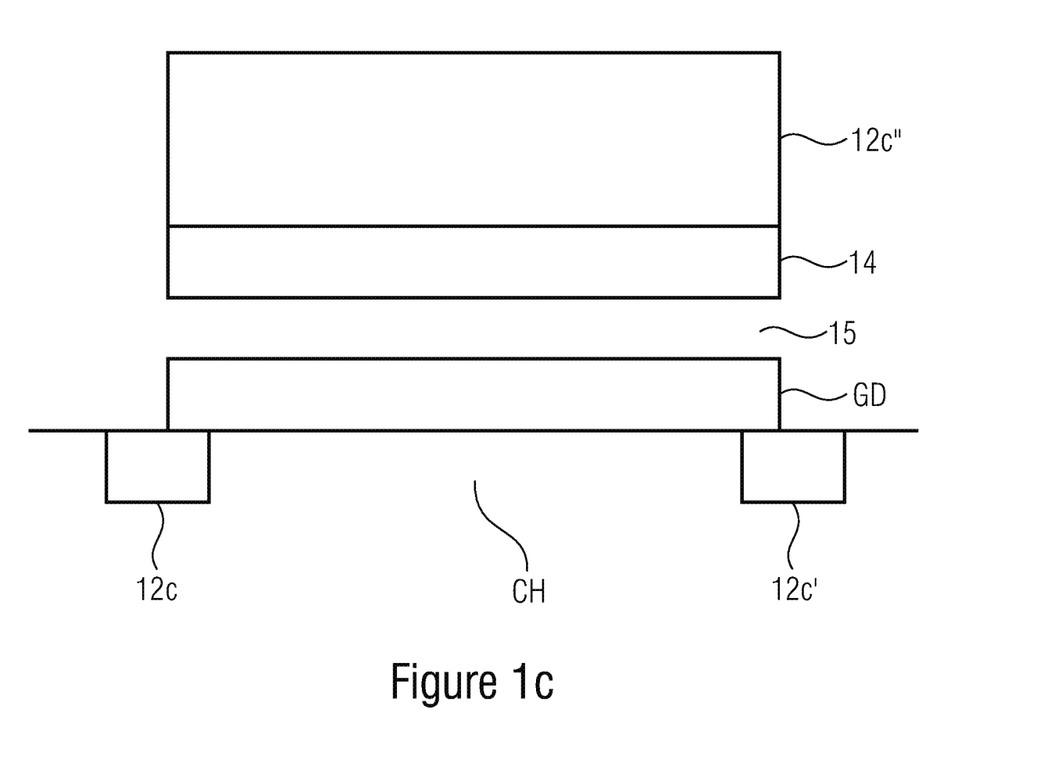

The electrodes 12a' and 12b' may be made of any conducting materials (for example an inorganic conductor, an organic conductor or a mixed organic/inorganic conductor), advantageously a metal or a conducting polymeric material, more advantageously a metal selected from the group of Ni, Au, Ag, Pt, or combinations thereof FIG. 1c shows an further embodiment. Here, the sensor device comprises a field effect transistor with a pair of source/drain regions 12c, 12c' in a semiconductor substrate, a channel CH, a gate dielectric GD and a suspended gate electrode 12c'', wherein the hybrid sensing material 14 (coating) is positioned between the channel CH and the gate electrode 12c''. Due to the dielectric behaviour of the sensitive layer 14 in the presence of $CO_2$, the source/drain current in the channel CH is changed so that an electrical signal responsive to the $CO_2$ concentration may be output by the transducer (i.e. field effect transistor 12c, 12c', 12c'', GD, CH). Advantageously, a gas inlet 15 is between the hybrid sensing material 14 and the gate dielectric CH.

The gate electrode 12c'' may be made of any conducting materials (for example an inorganic conductor, an organic conductor or a mixed organic/inorganic conductor), advantageously a metal or a conducting polymeric material, more advantageously a metal selected from the group of Ni, Au, Ag, Pt, or combinations thereof. Any semiconductor material may be used for the semiconductor substrate, e.g. Si, GaAs, Ge.

Figure 1D:
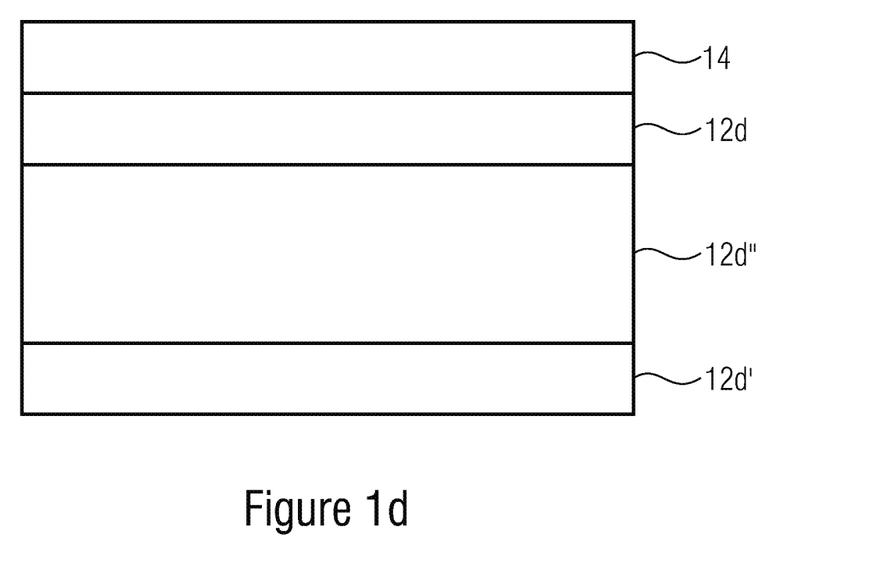

FIG. 1d shows a further embodiment. Here, the sensor device comprises a quartz crystal microbalance comprising an upper electrode 12d, a lower electrode 12d' and a quartz crystal plate 12d'' positioned between the upper and lower electrodes. The hybrid sensing material 14 is positioned on the upper electrode 12d. Due to the mass increase of the sensitive layer 14 in the presence of $CO_2$, a resonator frequency shift of the quartz crystal plate is used to measure the $CO_2$ concentration.

The electrodes 12d and 12d' may be made of any conducting materials (for example an inorganic conductor, an organic conductor or a mixed organic/inorganic conductor), advantageously a metal or a conducting polymeric material, more advantageously a metal selected from the group of Ni, Au, Ag, Pt, or combinations thereof. Any quartz material may be used for the quartz plate 12d''.

Figure 1E:
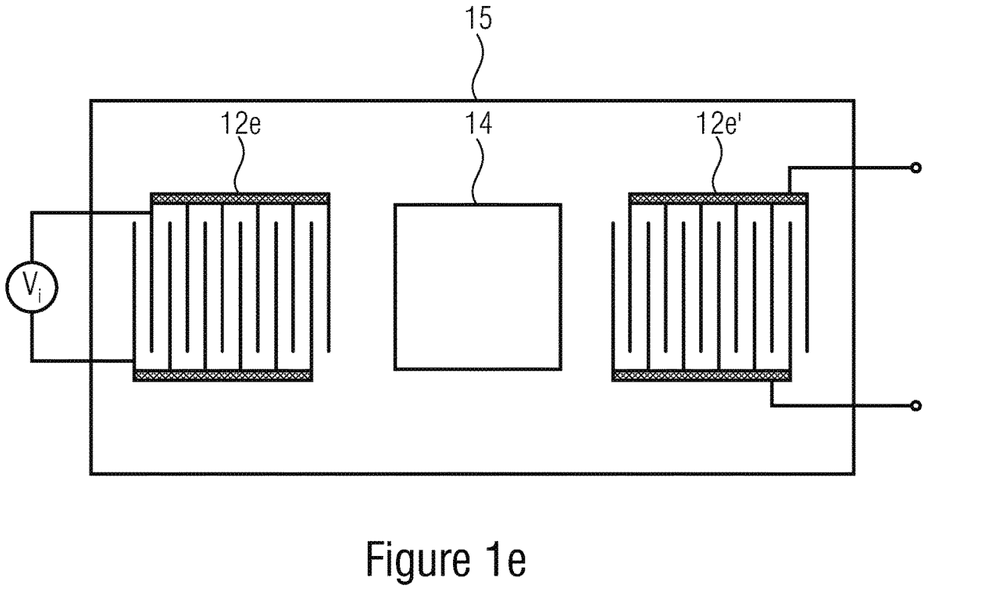

FIG. 1e shows a top view of further embodiment. Here, the sensor device comprises a surface acoustic wave sensor that comprises a piezoelectric substrate 15, a first pair of interdigitated electrodes 12e, a second pair of interdigitated electrodes 12e'. The first pair 12e is connected to a voltage source $V_i$. The hybrid sensing material 14 is positioned on the piezoelectric substrate 15 between the first and second pairs 12e, 12e'. The voltage source $V_i$ applies an input signal to the first pair of interdigitated electrodes 12e, that transform the input signal into a mechanical wave on the surface of the piezoelectric substrate 15. The mechanical wave propagates towards the second pair of interdigitated electrodes 12e'. The second pair 12e' converts the mechanical wave back into an electrical signal. Due to the mass increase of the sensitive layer 14 in the presence of $CO_2$, the mechanical wave propagation change is reflected in the output electrical signal of the second pair of interdigitated electrodes 12e'.

The electrodes 12e and 12e' may be made of any conducting materials (for example an inorganic conductor, an organic conductor or a mixed organic/inorganic conductor), advantageously a metal or a conducting polymeric material, more advantageously a metal selected from the group of Ni, Au, Ag, Pt, or combinations thereof. Any piezoelectric material may be used for the piezoelectric substrate 15.

Figure 1F:
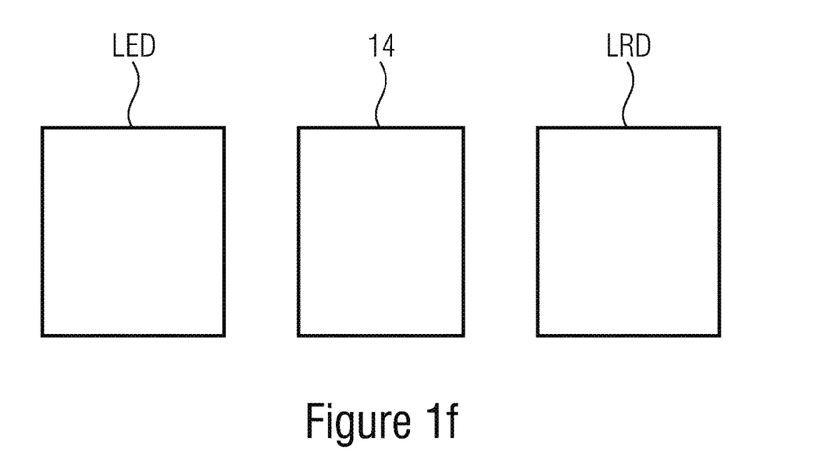

FIG. 1f shows a further embodiment, Here, the sensor device may comprise a light emitting device LED (e.g. a light emitting diode or a laser), a light receiving device LRD (e.g. a photodiode). The hybrid sensing material 14 is positioned between the light receiving device LED and the light emitting device LRD so that the light beam emitted by the light emitting device LED propagates through the hybrid sensing material 14 and is received by the light receiving device LRD. Due to the dielectric behaviour of the sensitive layer 14 in the presence of $CO_2$, the optical transmission of the hybrid sensing material is changed so that an optical signal detected by the light receiving device LRD changes.

Figure 2:
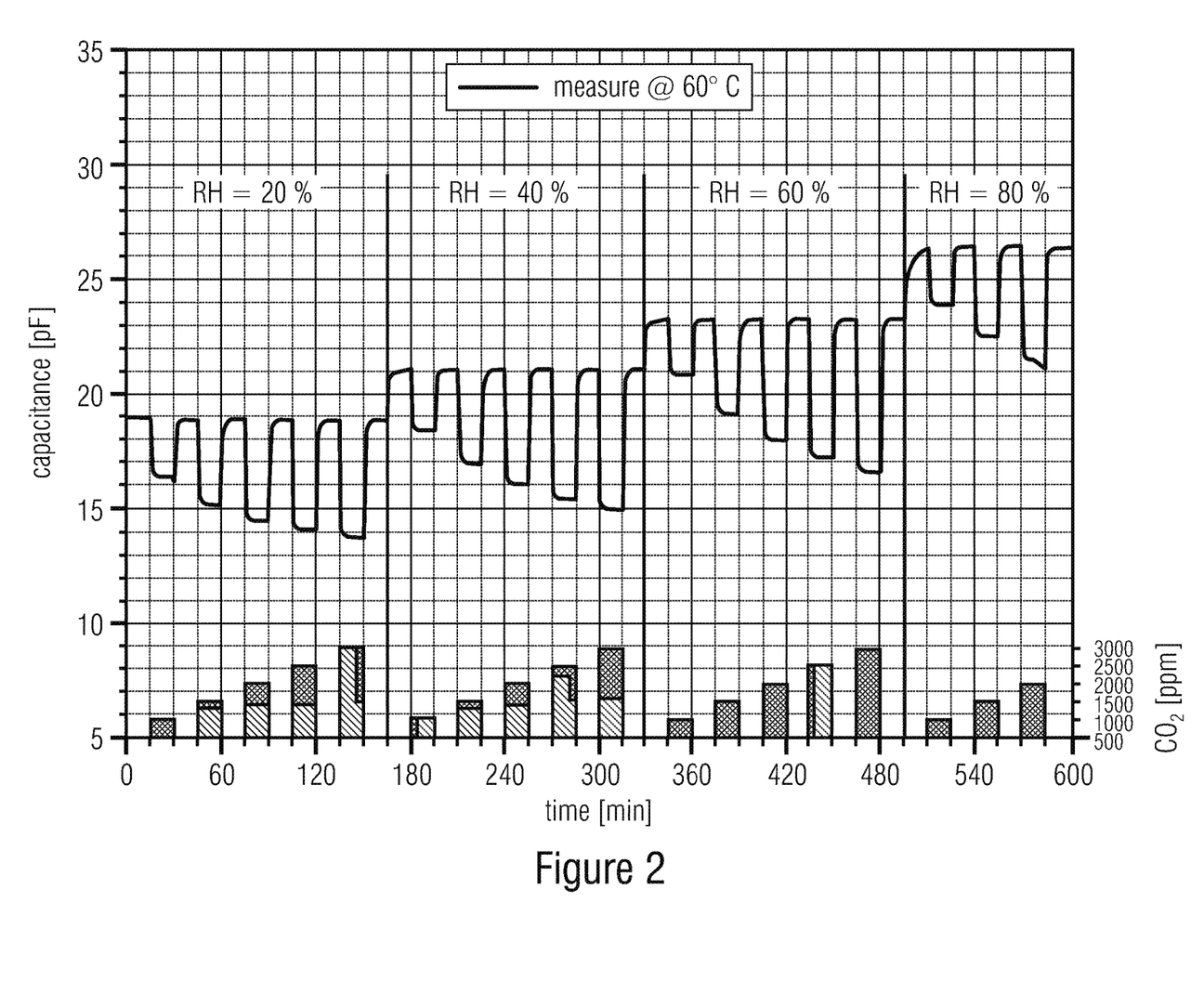
FIG. 2 shows an exemplary diagram illustrating the capacitance change of hybrid layer as a function of relative humidity changes and $CO_2$ concentration changes.

This relationship between the resent $CO_2$ concentration and the measured electrical sensor signal will be discussed referring to FIG. 2. FIG. 2 shows for example the sensor response—for example capacitance C in pF—to a $CO_2$ concentration at 60° C. for different relative humidity levels RH. For the device of FIG. 2, interdigitated gold microelectrodes are formed on a glass substrate so as to form a chip. Each chip consists of an interdigitated electrodes, a heater and a temperature sensor. The chip was glued and gold wire bonded to a designed printed circuit board (PCB). The hybrid sensing material comprising PEI as amines and $SiO_2$ nanoparticles having a diameter of 300 nm is coated between the gold microelectrodes. The prepared solution (comprising solvent with PEI and $SiO_2$ nanoparticles) is dispensed on gold interdigitated electrodes of the transducer on glass substrate by spin coating technique. Although spin coating was used in the example of FIG. 2, any other deposition technique can be used.

The $CO_2$ detection setup is based on impedimetric measurements. The impedance, in our case the capacitance, is monitored as a function of time with an Agilent HP impedance analyzer. The sensor is inserted in a zero force insertion adapter to connect the electrodes of the PCB. Then, it is entered in a circular chamber. The measurement chamber can retain 10 samples on chamber holders and characterize them under the same conditions. The desired relative humidity inside the measurements chamber is controlled with a commercially available Sensirion humidity sensor.

The gas stream consisting of a mixture of synthetic air, $CO_2$ and water vapor is introduced and distributed radially into the circular chamber. The whole chamber and pipe lines were heated to an appropriate temperature to avoid water condensation on the pipes walls.

The sensor was heated to 60° C. by applying a voltage to the integrated heater on the transducer. The capacitance value is measured under the defined gas stream having different concentrations of $CO_2$. The sensor sensitivity is evaluated by recording change in film capacitance with respect to base line in this case (RH/$CO_2$):(20%/500 ppm), see FIG. 2. $CO_2$ fluxes of different concentrations were introduced in a step-wise way in the chamber ("dynamic mode"). For each relative humidity level, the response of the sensor for $CO_2$ concentrations in the range 500-3000 ppm was traced. At high relative humidity levels (RH=60% and RH=80%) a slight drift of the base line capacitance could be observed.

The response time is calculated from the capacitance decrease when introducing the synthetic air/$CO_2$ mixture at a desired relative humidity inside the chamber. The recovery time of the capacitive sensors was determined by cutting off the $CO_2$ flow (500 ppm) and introducing only synthetic air at a desired relative humidity concentration. The response and recovery times were determined at $t_{90}$ to be less than 2 min. $t_{90}$ describes the time needed for the signal to attain 90% of the difference between two states.

The response curves reveal a correlation between the sensor capacitance, $CO_2$ amount and RH level in the surrounding environment. The capacitance value increases by increasing RH from 20 to 80% at a constant $CO_2$ concentration. The delta capacitance depending on relative humidity is of 1 pf/10% RH. Increasing the $CO_2$ concentration above 500 ppm leads to a decrease in the capacitance. Each $CO_2$ concentration from 500 to 3000 ppm has its own fingerprint regarding capacitance values. The sensing behavior of the $CO_2$ sensor monitored under different concentrations of $CO_2$ and RH levels confirms the reversibility of the hybrid sensitive layer. Therefore, the developed hybrid nanomaterial shows great potential for various applications involving $CO_2$ detection, including indoor air quality control.

With regard to the embodiments of FIGS. 1a to 1f it should be noted that the sensor device 10 may optionally comprise additional elements like a heater (cf. reference numeral 16) or a temperature sensor (not shown). The heater and/or temperature sensor may be positioned laterally with respect to the transducer (as illustrated in FIG. 1b) or vertically below the transducer (as illustrated in FIG. 1a) or vertically above the transducer. The relative positions are not limited as long as the heater and temperature sensor function in the desired way. Both enable to operate the $CO_2$ sensor 10 within the proper temperature range. The sensing temperature is advantageously between, i.e., −30° C. to 200° C. The temperature range plays a role with regard to the power consumption as well as with regard to the response and recovery times.

The above characterized $CO_2$ sensor 10 uses the electrical power to detect $CO_2$ (cf. reference numeral 11), for example, in the range between 500 ppm and 10,000 ppm. The transducer power consumption mainly results from the heater 16 used to reach the desired working temperature. Increasing the sensor operating temperature from room temperature to 60° C. increases the power consumption to some mW. Therefore, the $CO_2$ sensor 10 can target mainly applications going from indoor air control to automotive applications.

The above mentioned properties, especially with regard to the response and recovery times, the accuracy, particularly for sensing at room temperature and the energy demand, result from the material used as sensitive layer 14. As discussed above, the material for the sensitive layer 14 is a so-called hybrid (organic-inorganic) material comprising nano particles 20 and amines 22, e.g. in the shape of a polymer containing functional amine groups. Alternately, the sensitive layer 14 may comprise further polymers to achieve a homogenous stable mixture.

The developed hybrid material combining organic and inorganic material will be discussed below in detail. It should be noted here that discussion below belongs to the embodiments, wherein other implementations may also be possible.

The layer 14 responds to a small change in the concentration of carbon dioxide 11 in its vicinity by changing its electrical properties, impedance, capacitance, resistance, dielectric constant. As, for example, a capacitance variation takes place as a consequence of a change in the $CO_2$ concentration, a simple electronic circuit can be used to evaluate the sensor signal.

Amine based solid sorbents are one way to detect $CO_2$ in gas phase. Several polymers containing amino groups (see Table) were tested as sensitive layer to detect $CO_2$. The used polymer layer comprises two or more amine based polymers which can contain primary and/or secondary amines.

| Polymer having amine groups |
| --- |
| 3-aminopropyltrimethoxysilane (APTMS) |
| 3-Aminopropyl)triethoxysilane (APTES) |
| N-[3-(trimethoxysilyl) propyl]-ethylenediamine (AEAPTS) |
| Polypropyleneimine (PPI) |
| mono (di)ethanolamine (MEA (DEA)) |
| Polyethyleneimine (PEI) |
| 2-diethylamino-ethanol (DEEA) |
| 1,4 diaminobutane (DAB) |
| 1,3-propanediamine (DIAP) |
| 2,2-dimethyl-1,3-propanediamine (DMPDA) |
| 1-piperazineethanol (HEP) |
| 2-diisopropylamino-ethanol (DIPAE) |
| N,N,N',N'-tetrabutyl-3-oxapentanediamide (N-TBDA) |
| N1-methyl-1,3-Propanediamine (MAPA) |
| Polyallylamine (PAA) |
| Tetraethylenepentamine (TEPA) |

Figure 3:
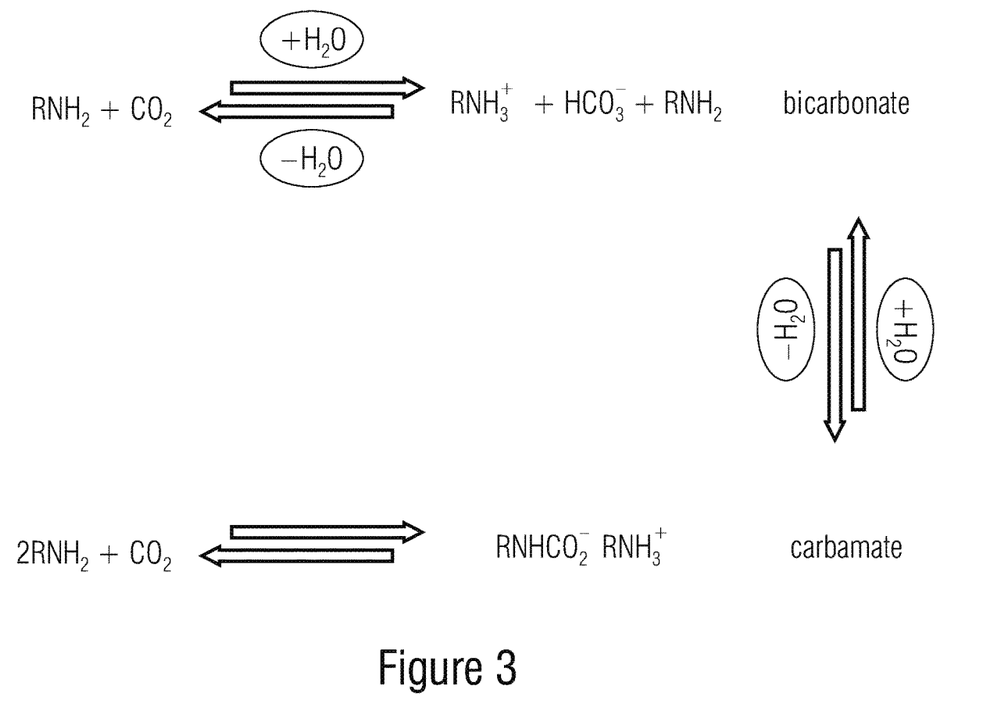
FIG. 3 shows an exemplary chemical reaction of $CO_2$ with primary amine groups in the present sense and absence of water.

The reaction mechanism of polymer containing primary amino groups with $CO_2$ is based on the reversible formation of carbonate or bio carbonate products, as illustrated by FIG. 3. FIG. 3 shows two chemical reactions of $CO_2$ with primary amino groups in their presence or absent of water.

The reaction takes place by an interaction between the adsorbate molecule $CO_2$ and the functional group on the adsorbents surface. A physisorption interaction occurs due to van der Waals forces, which are rather weak and ensure a fast desorption process. A chemisorption process is related to a chemical interaction, which is more stable and under these conditions irreversible involving a high temperature desorption step.

Advantageously, the nanoparticles may be selected from $SiO_2$, $Al_2O_3$, $TiO_2$, $ZrO_2$, and the like, and combinations thereof. The nanoparticles diameter may be in the range from 10 to 500 nm, advantageously in the range from 150 nm to 400 nm.

Advantageously, in the hybrid sensing material, the ratio between the total weight of nanoparticles and the total weight of polymer-based amines is in the range from 1:5 to 5:1.

Figure 4:
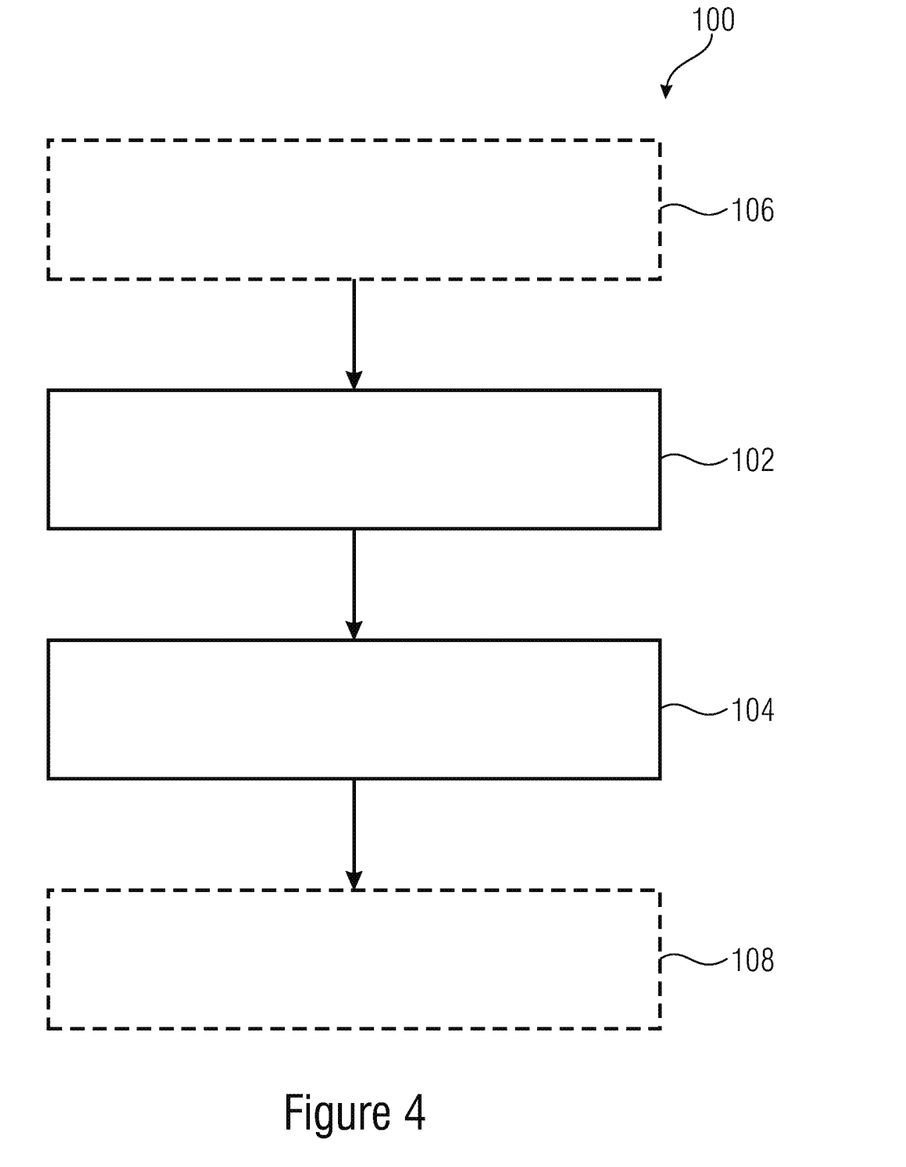
FIG. 4 shows an exemplary flow chart illustrating the method for manufacturing the sensor device according to FIGS. 1a to 1f.

Below, the method for manufacturing the sensor 10 of FIGS. 1a to 1f will be discussed in detail taking reference to the flow chart of FIG. 4. FIG. 4 shows the method for manufacturing 100 comprising the two basic steps 102 of providing the transducer and 100 for providing the sensitive layer.

The transducer 12 may be provided on a substrate (glass or any other suitable material) or may comprise a substrate. After providing the transducer (step 102) carbon dioxide-sensitive material is provided, advantageously on top of the transducer 12 (see e.g. FIG. 1d) or in between the respective electrodes, see for example FIGS. 1a, 1b, 1c, 1e (cf. step 104). The providing of the sensitive layer 14 may be done by using deposition methods such as drop in, spin coating, spray coating, dip coating, doctor blade or other known deposition methods to coat an element like a transducer. Some of these methods involve that the hybrid sensitive material, or in more detail, the nano particles and the amines are dispersed in an appropriate solvent before same can be provided. Therefore, the method 100 may comprise an optional step 106 of dispersing the hybrid sensitive material in a solvent.

In order to immobilize the hybrid sensitive material, e.g., on the transducer, the manufacturing method 100 may comprise a step of drying 108 subsequent to the step 104 of providing the hybrid sensitive material.

The method for manufacturing will be discussed in detail below, wherein the features discussed below are just design variants of the basic method 100 discussed above, i.e., optional features.

Here, inorganic nanoparticles are used with, for example, surface-exposed —OH groups which facilitate the functionalization with amine based polymers. Therefore, the amine groups can be strongly attached to the nanoparticles surface via covalent or ionic bonding, depending on the nature of the polymer containing the amino-functionalized extremity. A stable immobilization is desired to ensure thermal stability of the amino-groups on the surface of the nanoparticles at temperatures below the thermal decomposition temperatures of the used polymer.

The nanoparticles (like $SiO_2$, $Al_2O_3$, $TiO_2$, $ZrO_2$, . . . ) are dispersed in an appropriate solvent (e.g. water, ethanol, methanol, etc.) and mixed with one or several polymer-based amino-groups under vigorous stirring for a time needed to get a homogeneous mixture. To achieve a bonding between the nanoparticles and the amino-groups, the stirred solution undergoes a drying step (e.g. under vacuum) for some hours. The resulting material is powdered and contains amine groups impregnated or grafted on the surface of the nanoparticles. The ratio of applied nanoparticles to amino-polymer determines the density of amine groups on the nanoparticles surface. This ratio is adjustable depending on the desired application. The nanoparticles and the polymeric chains can be selected from various commercially available materials. To coat the transducer, the prepared amine functionalized nanoparticles may be diluted in an appropriate solvent (e.g. water, ethanol, methanol, etc.) and then it may be dispended on the electrodes and it may be dried under appropriate condition and at temperatures, for example, between 60° C. to 200° C. for some time (e.g. 5 minutes-5 h).

According to another embodiment the above discussed hybrid sensing material or the above discussed sensor is configured to change the electrical or optical property dependent on a H2O concentration in the surrounding. This means that the above discussed device, e.g. with the interdigitated electrodes coated with a layer containing the sensing material, reacts at once on humidity (H2O) and on CO2. The capacitance increases if the humidity levels increase at a fixed CO2 concentration. However, at a fixed humidity level, the capacitance decreases by increasing the CO2 amount in our surrounding environment. Thus, the electrical or optical property change as response to a CO2 concentration differs from the electrical or optical property change as response to a H2O concentration.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such altera-

REFERENCES

[1] http://www.theboc.info/pdf/Article-Measuring_C02_Inside_Buildings-Jan2013.pdf

[2] N. Gravenstein et al., Capnography and the Bain Circuit (1984)

[3] Guidelines for Emissions Monitoring and Reporting in the Cement Industry (2012)

[4] European F-gas Regulation, 2014. http://ec.europa.eu/clima/policies/f-gas/index_en.htm

[5] T. Labeodan et al., Energy and Buildings 93 (2015) 303-314

[6] http://www.euractiv.com/sections/energy/europes-energy-union-needs-carbon-capture-and-storage-312387

[7] J. Hodgkinsona et al., Sensors and Actuators B: Chemical, V. 186 (2013) P: 580-588

[8] R. Moos et ai., Sensors, 9, (2009) 4323-4365

[9] G. F. Fine et al., Sensors 10 (2010), 5469-5502.

The invention claimed is:

1. A sensor device for sensing $CO_2$, comprising:
   a hybrid sensing material comprising a mixture of at least amines and nanoparticles, wherein the hybrid sensing material comprises an electrical or optical property and is configured to change the electrical or optical property dependent on a $CO_2$ concentration in the surrounding; and
   a transducer configured to output an electrical sensor signal dependent on the electrical or optical property of the hybrid sensing material, the property is an electrical or optical property out of a group comprising impedance, capacitance and optical transmission.

2. The sensor device according to claim 1, wherein the transducer comprises two electrodes, wherein at least one electrode is coupled to the hybrid sensing material in order to detect the electrical or optical property of the hybrid material.

3. The sensor device according to claim 2, wherein the hybrid sensing material is arranged between the two electrodes and/or is arranged on top of said at least one electrode.

4. The sensor device according to claim 2, wherein the electrodes comprise any conducting material or a metal or a conducting polymeric material, or a metal selected from the group of Ni, Au, Ag, Pt, or combinations thereof.

5. The sensor device according to claim 1, wherein the transducer comprises a field effect transistor with a pair of source/drain regions, a channel and a suspended gate electrode, wherein the hybrid sensing material is positioned between the channel and the suspended gate electrode.

6. The sensor device according to claim 1, wherein in transducer comprises an upper electrode, a lower electrode and a quartz plate positioned between the upper and lower electrodes, wherein the hybrid sensing material is positioned on the upper electrode.

7. The sensor device according to claim 1, wherein the transducer comprises a piezoelectric substrate, a first pair of interdigitated electrodes, a second pair of interdigitated electrodes on said piezoelectric substrate, wherein the first pair of interdigitated electrodes is connected to a voltage source, and wherein the hybrid sensing material is positioned on the piezoelectric substrate between the first and second pairs of interdigitated electrodes.

8. The sensor device according to claim 1, wherein the transducer comprises a light emitting device, a light receiving device, wherein the hybrid sensing material is positioned between the light receiving device and the light emitting device so that the light beam emitted by the light emitting device propagates through the hybrid sensing material and is received by the light receiving device.

9. The sensor device according to claim 1, further comprising a heater for heating the hybrid sensing material.

10. The sensor device according to claim 1, wherein the hybrid sensing material reacts with $CO_2$ in accordance with the formula or in accordance with the formula 11. The sensor device according to claim 1, wherein the electrical sensor signal is indicative for a measured impedance or capacitance; wherein an increase of the $CO_2$ concentration leads to a change of the impedance or capacitance.

12. The sensor device according to claim 1, wherein the electrical sensor signal is dependent on the $CO_2$ concentration in the surrounding and on the relative humidity in the surrounding.

13. The sensor device according to claim 1, wherein the hybrid sensing material comprises organic and inorganic compounds.

14. The sensor device according to claim 1, wherein the hybrid sensing material comprises a polymer or polymer-based amines.

15. The sensor device according to claim 1, wherein the amines are out of a group comprising primary amino groups and secondary amino groups.

16. The sensor device according to claim 1, wherein the amines are out of a group comprising: 3-aminopropyltrimethosysilane; APTMS; 3-Aminopro(pyl)triethoxysilane; APTES; Polypropyleneimine; PPI; mono(di)ethanolamine MEA; DEA; Polyethyleneimine; PEI; 2-diethylamino-ethanol; DEEA; 1,4-diaminobutane; DAB; 1,3-propanediamine; DiAP; 2,2-dimethyl-1,3-propanediamine; DMPDA; 1-piperazineethanol; HEP; 2-diisopropylamino-ethanol; DIPAE; N,N,N',N'-tetrabutyl-3-oxapentanediamide; N-TBDA; N1-methyl-1,3-Propanediamine; MAPA; and Polyallylamine; PAA.

17. The sensor device according to claim 16, wherein the electrical or optical property change as response to a $CO_2$ concentration differs from the electrical or optical property change as response to a $H_2O$ concentration.

18. The method according to claim 17, wherein providing the hybrid sensing material is performed using coating or drop in, coating, spray coating, dip coating, doctor blade on the transducer or on a substrate comprising the transducer.

19. The sensor device according to claim 1, wherein the hybrid sensing material is configured to change the electrical or optical property dependent on a $H_2O$ concentration in the surrounding.

20. A method for manufacturing a sensor device for sensing $CO_2$, comprising:
   providing a transducer configured to output an electrical sensor signal dependent on a electrical or optical property of a hybrid sensing material; and
   providing the hybrid sensing material comprising at least amines and nanoparticles, wherein the hybrid sensing material comprises an electrical or optical property and is configured to change the electrical or optical property dependent on a $CO_2$ concentration in the surrounding, where the property is an electrical or optical property out of a group comprising impedance, capacitance and optical transmission;

further comprising dispersing the amines and the nanoparticles or polymer-amines and the nanoparticles by usage of a solvent before providing the hybrid sensing material; wherein dispersing is performed using mixing the solvent under stirring.

21. The method according to claim 20, further comprising drying the solvent after providing the hybrid sensing material.

22. A coating comprising a hybrid sensing material for sensing $CO_2$ comprising a mixture of at least amines and nanoparticles, wherein the hybrid sensing material comprises an electrical or optical property and is configured to change the electrical or optical property dependent on a $CO_2$ concentration in the surrounding, wherein the nanoparticles comprise one material out of the group comprising $SiO_2$, $Al_2O_3$, $TiO_2$, $ZrO_2$, and combinations thereof.

23. A sensor device for sensing $CO_2$, comprising:
a hybrid sensing material comprising a mixture of at least amines and nanoparticles, wherein the hybrid sensing material comprises an electrical or optical property and is configured to change the electrical or optical property dependent on a $CO_2$ concentration in the surrounding; and
a transducer configured to output an electrical sensor signal dependent on the electrical or optical property of the hybrid sensing material;
wherein in transducer comprises an upper electrode, a lower electrode and a quartz plate positioned between the upper and lower electrodes, wherein the hybrid sensing material is positioned on the upper electrode; or
wherein the transducer comprises a piezoelectric substrate, a first pair of interdigitated electrodes, a second pair of interdigitated electrodes on said piezoelectric substrate, wherein the first pair of interdigitated electrodes is connected to a voltage source, and wherein the hybrid sensing material is positioned on the piezoelectric substrate between the first and second pairs of interdigitated electrodes; or
wherein the transducer comprises a light emitting device, a light receiving device, wherein the hybrid sensing material is positioned between the light receiving device and the light emitting device so that the light beam emitted by the light emitting device propagates through the hybrid sensing material and is received by the light receiving device.

24. A sensor device for sensing $CO_2$, comprising:
a hybrid sensing material comprising a mixture of at least amines and nanoparticles, wherein the hybrid sensing material comprises an electrical or optical property and is configured to change the electrical or optical property dependent on a $CO_2$ concentration in the surrounding; and
a transducer configured to output an electrical sensor signal dependent on the electrical or optical property of the hybrid sensing material;
further comprising a heater for heating the hybrid sensing material.

25. A sensor device for sensing $CO_2$, comprising:
a hybrid sensing material comprising a mixture of at least amines and nanoparticles, wherein the hybrid sensing material comprises an electrical or optical property and is configured to change the electrical or optical property dependent on a $CO_2$ concentration in the surrounding; and
a transducer configured to output an electrical sensor signal dependent on the electrical or optical property of the hybrid sensing material;
wherein the electrical sensor signal is dependent on the $CO_2$ concentration in the surrounding and on the relative humidity in the surrounding; or
wherein the hybrid sensing material is configured to change the electrical or optical property dependent on a $H_2O$ concentration in the surrounding, where the property is an electrical or optical property out of a group comprising impedance, capacitance and optical transmission; or
wherein the electrical or optical property change as response to a $CO_2$ concentration differs from the electrical or optical property change as response to a $H_2O$ concentration, where the property is an electrical or optical property out of a group comprising impedance, capacitance and optical transmission.

26. A sensor device for sensing $CO_2$, comprising:
a hybrid sensing material comprising a mixture of at least amines and nanoparticles, wherein the nanoparticles comprise one material out of the group comprising $SiO_2$, $Al_2O_3$, $TiO_2$, $ZrO_2$, and combinations thereof;
wherein the hybrid sensing material comprises an electrical or optical property and is configured to change the electrical or optical property dependent on a $CO_2$ concentration in the surrounding; and
a transducer configured to output an electrical sensor signal dependent on the electrical or optical property of the hybrid sensing material.

* * * * *

UNITED STATES PATENT AND TRADEMARK OFFICE
CERTIFICATE OF CORRECTION

PATENT NO. : 11,435,308 B2
APPLICATION NO. : 16/053506
DATED : September 6, 2022
INVENTOR(S) : Jamila Boudaden and Benjamin Gruber It is certified that error appears in the above-identified patent and that said Letters Patent is hereby corrected as shown below:

In the Claims

Column 12, Claim 18:
Delete "18. The method according to claim 19, wherein providing the hybrid sensing material is performed using coating or drop in, coating, spray coating, dip coating, doctor blade on the transducer or on a substrate comprising the transducer."

Column 12, Claim 19:
Delete "19." and change to --18.--

Column 12, Claim 20:
Delete "20." and change to --19.--

Column 13, before Claim 21:
Insert --20. The method according to claim 19, wherein providing the hybrid sensing material is performed using coating or drop in, coating, spray coating, dip coating, doctor blade on the transducer or on a substrate comprising the transducer.--

Column 13, Claim 21:
Delete "The method according to claim 20," and change to --The method according to claim 19,--

Signed and Sealed this
Fifth Day of December, 2023

Katherine Kelly Vidal
*Director of the United States Patent and Trademark Office*